(12) United States Patent
Piana et al.

(10) Patent No.: US 9,995,691 B2
(45) Date of Patent: Jun. 12, 2018

(54) DEVICE AND METHOD FOR CONTINUOUSLY INSPECTING CONTAINERS

(71) Applicant: KRONES AG, Neutraubling (DE)

(72) Inventors: Stefan Piana, Koefering (DE); Stefan Richter, Thalmassing (DE)

(73) Assignee: Krones AG, Neutraubling (DE)

( * ) Notice: Subject to any disclaimer, the term of this patent is extended or adjusted under 35 U.S.C. 154(b) by 0 days. days.

(21) Appl. No.: 15/534,422

(22) PCT Filed: Oct. 9, 2015

(86) PCT No.: PCT/EP2015/073351
§ 371 (c)(1),
(2) Date: Jun. 8, 2017

(87) PCT Pub. No.: WO2016/102092
PCT Pub. Date: Jun. 30, 2016

(65) Prior Publication Data
US 2017/0343483 A1    Nov. 30, 2017

(30) Foreign Application Priority Data

Dec. 23, 2014    (DE) .................. 10 2014 226 965

(51) Int. Cl.
*G01N 21/90*    (2006.01)
*B65G 47/244*    (2006.01)
(Continued)

(52) U.S. Cl.
CPC ......... *G01N 21/9009* (2013.01); *B65G 17/26* (2013.01); *B65G 23/23* (2013.01);
(Continued)

(58) Field of Classification Search
CPC ..... G01N 21/9009; B65G 23/23; B65G 17/26
(Continued)

(56) References Cited

U.S. PATENT DOCUMENTS

| 3,797,632 | A |   | 3/1974 | Riggs |   |
|---|---|---|---|---|---|
| 5,551,348 | A | * | 9/1996 | Matsumoto | .............. B23Q 7/14 104/88.02 |

(Continued)

FOREIGN PATENT DOCUMENTS

| DE |   | 3415383 A1 | 11/1985 |
|---|---|---|---|
| DE | 102004048515 A1 |   | 4/2006 |

(Continued)

OTHER PUBLICATIONS

ISA European Patent Office, International Search Report Issued in Application No. PCT/EP2015/073351, dated Jan. 5, 2016, WIPO, 6 pages.

*Primary Examiner* — Roy M Punnoose
(74) *Attorney, Agent, or Firm* — McCoy Russell LLP

(57) ABSTRACT

The present disclosure provides an inspection device for continuously inspecting fed containers, in particular bottles, said inspection device comprising a feed device configured to feed containers thereto in succession, at least one inspection unit, configured to inspect the fed containers, a discharge conveying device configured to discharge the inspected containers, and a throughput station for the containers, which is arranged between the feed conveying device and the discharge conveying device, wherein the throughput station comprises a conveyor arrangement with an individual drive and a plurality of conveying units, which are movable by means of the individual drive individually and independently of one another, the conveyor arrangement being configured to convey the containers from the feed conveying device to the discharge conveying device.

14 Claims, 8 Drawing Sheets

(51) Int. Cl.
*B65G 17/26* (2006.01)
*B65G 23/23* (2006.01)
*G01N 21/84* (2006.01)

(52) U.S. Cl.
CPC .. *B65G 47/2445* (2013.01); *B65G 2201/0244* (2013.01); *B65G 2207/08* (2013.01); *G01N 2021/845* (2013.01); *G01N 2201/062* (2013.01)

(58) Field of Classification Search
USPC ....................................................... 356/240.1
See application file for complete search history.

(56) References Cited

U.S. PATENT DOCUMENTS

| | | | | |
|---|---|---|---|---|
| 9,809,392 | B2* | 11/2017 | Walter | B65G 37/02 |
| 2016/0114988 | A1* | 4/2016 | Unterseher | B65G 54/02 |
| | | | | 198/465.1 |
| 2016/0214799 | A1* | 7/2016 | Walter | B65G 37/02 |

FOREIGN PATENT DOCUMENTS

| | | |
|---|---|---|
| DE | 102012201059 A1 | 7/2013 |
| EP | 0415154 A1 | 3/1991 |
| EP | 2511203 A1 | 10/2012 |
| GB | 2325204 A | 11/1998 |
| JP | S62285817 A | 12/1987 |
| JP | 2014024665 A | 2/2014 |
| WO | 2008022296 A2 | 2/2008 |

* cited by examiner

DEVICE AND METHOD FOR CONTINUOUSLY INSPECTING CONTAINERS

CROSS-REFERENCE TO RELATED APPLICATIONS

The present application is a U.S. National Phase of International Patent Application Serial No. PCT/EP2015/073351 entitled "DEVICE AND METHOD FOR CONTINUOUSLY INSPECTING CONTAINERS," filed on Oct. 9, 2015. International Patent Application Serial No. PCT/EP2015/073351 claims priority to German Patent Application No. 10 2014 226 965.2, filed on Dec. 23, 2014. The entire contents of each of the above-referenced applications are hereby incorporated by reference for all purposes.

FIELD OF THE INVENTION

The present invention relates to a device and a method for continuously inspecting containers, in particular bottles, e.g. for empties inspection in the beverage industry.

PRIOR ART

Inspection machines are used e.g. in the beverage industry for examining empties, such as glass or plastic bottles, for damage, contamination or residues of liquid before the examined containers are returned to the product cycle. In so doing, the containers to be inspected must be guided, at least temporarily, such that the bottom area and the outlet area are freely accessible simultaneously. This allows inspection by transmitted light in the direction of the main axis of the container, whereby e.g. the container bottom can be inspected with respect to damage or a residue of liquid contained in the container can be detected by infrared. Inspection is here normally carried out in a fully automatic manner with the aid of suitable optical systems, e.g. by making use of a camera and an LED flash lamp, and with the aid of a suitable evaluation software, which draws conclusions from the measurement data and image data, respectively, with respect to the above-mentioned damage and contamination. Damaged and/or contaminated containers can then be discharged automatically and subjected to further processing and/or cleaning.

Linear inspection machines known from the prior art comprise a throughput station within which the containers are linearly conveyed by pressure applied from both sides via conveyor belts arranged on both sides. Since the containers are laterally held in the throughput station, the bottom area and the outlet area of the containers are freely accessible at the same time. An inspection machine comprising a conveyor belt in the area of the throughput station is known e.g. from EP 0 415 154 B1. The conveyor belts do not have defined positions for holding the containers, but they are able to pick up containers at arbitrary positions. A plurality of containers which are simultaneously present in the throughput station are here conveyed synchronously by the conveyor belts. Typically, rotationally symmetrical containers, such as bottles, are rotated by 90° about their container axis along the transit route, so that sidewall inspection units provided in the infeed and discharge areas of the inspection machine will be able to inspect respective different areas of the circumferential surface of the containers.

In the case of the inspection machines with belt conveyance in the throughput station known from the prior art, the containers must be fed pressureless, i.e. without being in contact with one another, in the container infeed. This necessitates the use of a complex and bulky device for pressure reduction, i.e. for spatially separating the containers that are normally conveyed in a mutually abutting mode, in the incoming container flow, e.g. by providing transfer elements, sawtooth star wheels or infeed worms. The frequently used transfer elements are not able to define a defined minimum distance so that segment-type discharge elements cannot be used. In addition, container rotation during conveyance by means of conveyor belts often has the effect that the containers tilt by a few degrees in the direction of movement, in particular if the holding area deviates from the ideal cylinder shape. This may impair the efficiency of inspections, e.g. for the container bottom or for screw threads, and guiding of the containers on the discharge side may become more difficult in the case of higher container throughput rates of the inspection machine.

Hence, it is the object of the present invention to provide a device and a method for continuously inspecting containers, which avoid the above-mentioned drawbacks. In particular, feeding the containers to and discharging them from the inspection machine is to be simplified. Furthermore, the conveying stability of the containers in the throughput station is to be increased so as to improve the efficiency of the inspection units. In addition, it is the object of the present invention to facilitate, in the case of the inspection machine used, a change of the type of containers.

DESCRIPTION OF THE INVENTION

The above-mentioned objects are achieved by an inspection device for continuously inspecting fed containers, in particular bottles, comprising: a feed conveying device configured to feed containers to the inspection device in succession, at least one inspection unit configured to inspect the fed containers, a discharge conveying device configured to discharge the inspected containers, and a throughput station for the containers, which is arranged between the feed conveying device and the discharge conveying device, the throughput station comprising a conveyor arrangement with an individual drive and a plurality of conveying units, which are movable by means of the individual drive individually and independently of one another, the conveyor arrangement being configured to convey the containers from the feed conveying device to the discharge conveying device.

The containers may be cans, glass bottles or other glass containers having a lid, plastic bottles, consisting e.g. of PET, or the like. In particular transparent containers, such as glass bottles or plastic bottles made of PET, can be inspected in an advantageous manner by the inspection device, since in the case of transparent objects not only the side facing the respective sensor or the respective camera but also the opposite side of the container can be detected and examined. On the basis of the sidewall inspection units described hereinafter, the whole circumferential surface of the container can thus be inspected by rotating the container in the throughput station.

According to the present invention, the inspection device comprises a feed conveying device for feeding the containers in succession, a discharge conveying device for discharging the inspected containers, and a throughput station for the containers, which is arranged between the feed conveying device and the discharge conveying device. For continuously inspecting the containers, the inspection device has fed thereto a flow of containers via the feed conveying device, the containers of said flow of containers being then conveyed by means of the conveyor arrangement described hereinafter along a conveying route connecting the feed conveying device to the discharge conveying device, whereupon they are discharged by the discharge conveying device. Within the throughput station, the containers are conveyed such that the bottom area and the outlet or top area of the conveyed containers are freely accessible at the same time. The feed conveying device and/or the discharge conveying device may be configured e.g. as conveyor belts conveying the containers under pressure, i.e. in a mutually abutting mode. Alternatively, also other conveying systems may be used, including the linear motor drives described hereinafter, but belt conveyance or infeed star wheels and/or discharge star wheels are imaginable as well. The systems referred to are sufficiently known in the prior art and will therefore not be explained in detail in the present context. Reference should only be made to the fact that the above-mentioned conveyor arrangement of the throughput station takes over the fed containers from the feed conveying device and transfers them to the discharge conveying device after conveyance through the throughput station. To this end, the containers, which are conveyed e.g. in an upright condition by the feed conveying device, can be taken off from a conveyor belt and raised, so that their bottom surface will become accessible for inspection. The conveyor arrangement may then put down the inspected containers on a conveyor belt of the discharge conveying device.

According to the present invention, the inspection device comprises at least one inspection unit for inspecting the fed containers. Said at least one inspection unit may be arranged in the area of the throughput station on the conveying route of the conveyor arrangement, on the feed conveying device or also on the discharge conveying device. In the area of the throughput station, e.g. an inspection unit for sealing surface inspection may be provided, which inspects an outlet area of the containers for damage by means of an illumination unit and a camera, e.g. a CCD camera. Alternatively or additionally, an inspection unit for liquid residue inspection, e.g. by means of high frequency and/or infrared, may be provided. As has already been mentioned, it is especially possible to provide an inspection unit for inspecting the container bottom, in the case of which a camera records an image of the container bottom, which is illuminated by an LED flash lamp. It is also imaginable to provide an inspection unit for inner sidewall inspection, in the case of which the interior of the container is inspected through the container outlet by means of a CCD camera. Other examples are inspection units for thread inspection or lateral outlet inspection, which inspect the outlet area of the containers. It goes without saying that the above-mentioned inspection units may have added thereto, or may be replaced by, other container inspection units known in the prior art.

In addition, the inspection units for sidewall inspection described in more detail hereinafter can be provided at the feed conveying device and/or the discharge conveying device. Furthermore, the feed conveying device may have provided thereat an inspection unit for foreign container detection by means of which foreign containers can be detected and discharged prior to entering the throughput station. The inspection units described execute the respective inspection steps in an at least partially automatic manner by detecting each container of the continuous flow of containers in the respective container area making use of sensors or of optical units. The detected sensor or image data can, moreover, be processed in a fully automatic manner, and detected defective containers can be discharged downstream of the inspection device.

According to the present invention, the containers are conveyed along the conveying route of the conveyor arrangement of the throughput station by means of an individual drive and a plurality of conveying units, which are movable by means of the individual drive individually and independently of one another. The term individual drive describes here and in the following a drive that drives the plurality of conveying units individually. The drive may be provided as part of the respective conveying unit and/or as a separate drive, which is configured such that the conveying units are movable individually and independently of one another. This independent movement relates to the position as well as to the speed of the conveying unit. The conveyor arrangement is provided with a plurality of individually movable conveying units. The conveying units are configured such that they are able to convey one or a plurality of containers along the conveying route with an individual displacement-time profile. In particular, the conveying units may be configured as carriages or runners, each of them provided with holding devices for conveying the containers. The individual drive may in particular be the linear motor drive, which will be described in more detail hereinafter and in the case of which the conveying units are moved individually and independently of one another via magnetic interaction with one or a plurality of linear stators. For defining the respective displacement-time profiles of the conveying units and thus of the conveyed containers, the inspection device according to the present invention may comprise an open-loop and/or closed-loop control unit as part of the conveyor arrangement, said open-loop and/or closed-loop control unit controlling the conveying units and/or the individual drive in a suitable manner. The number of conveying units may be chosen in accordance with the desired throughput of containers of the inspection device as well as depending on a length of the conveying route and of the conveyor tracks referred to hereinafter. Normally, the number of conveying units provided is at least large enough for allowing the necessary inspection steps to be carried out at the possibly more than one inspection unit preferably at a plurality of containers in parallel, and for preventing gaps in the continuous inspection.

According to a further development, the conveyor arrangement may comprise a first conveyor track having movably arranged thereon a first plurality of conveying units, and a second conveyor track having movably arranged on a second plurality of conveying units, said first conveyor track and said second conveyor track being arranged relative to one another and relative to the feed conveying device and the discharge conveying device such that, in the area of the throughput station, pairs of oppositely engaging conveying units for the containers can be formed, said pairs consisting each of a conveying unit of the first plurality of conveying units and of a conveying unit of the second plurality of conveying units.

The first and the second conveyor track may here extend beyond the area of the conveying route in the area of the throughput station. The first and second conveyor tracks may, in principle, have an arbitrary shape as long as a part of the two conveyor tracks is arranged between the feed conveying device and the discharge conveying device such that containers can be conveyed from the feed conveying device through the throughput station to the discharge conveying device. In particular, the conveyor tracks may be substantially closed, substantially closed meaning here that the respective conveyor track comprises at least one closed path for the respective plurality of conveying units. This may e.g. be realized by providing a feedback track as part of the conveyor track, said feedback track allowing the conveying units to be returned to the feed conveying device after transfer of the containers to the discharge conveying device. Each conveyor track may, however, also be configured such that it is partially open in such a way that at least a subsection of the conveyor track is configured as a dead end for buffering conveying units. Moreover, it is not necessary that the whole conveyor track in question is provided with the described individual drive for the conveying units. Alternatively, the part of the conveyor track outside the throughput station and, in particular, the feedback track may be provided with a continuous drive, such as a conveyor belt or the like.

The number of the conveying units movably arranged on the respective conveyor track depends on the number of containers to be conveyed simultaneously, i.e. on a predetermined throughput of containers per time interval for the inspection device. The number of conveying units arranged on the first conveyor track may especially correspond to the number of conveying units arranged on the second conveyor track, or, if necessary, it may differ therefrom.

According to this further development, the first and second conveyor tracks are arranged relative to one another and relative to the feed conveying device and the discharge conveying device such that, in the area of the throughput station, pairs of oppositely engaging conveying units for the containers can be formed, said pairs consisting each of a conveying unit of the first plurality of conveying units and of a conveying unit of the second plurality of conveying units. In particular, the first and second conveyor tracks are arranged such that the pairs of conveying units are formed at the beginning of the conveying route of the throughput station for taking up the containers from the feed conveying device, said pairs being maintained along the whole conveying route and de-established only at the end of the conveying route for transferring the containers to the discharge conveying device. The pairs are here formed and de-established in that the two conveyor tracks approach one another and diverge from one another at the locations in question.

The phrase forming a pair of conveying units should be understood here and in the following such that the two conveying units forming the respective pair are, by means of the individual drive and an open-loop and/or closed-loop control unit, positioned and moved along the respective conveyor track such that a pair is obtained through the spatial position of the conveying units relative to one another and relative to the conveying route. In particular, no mechanical coupling of the oppositely engaging conveying units will normally be necessary for forming the pairs.

The phrase oppositely engaging conveying units stands here for conveying units which are configured and oriented such that the containers can be conveyed between oppositely engaging conveying units and by means of mechanical contact with the latter such that the bottom area as well as the outlet area of the containers are freely accessible during conveyance. To this end, the conveying units act on a substantially cylindrical part of the container during conveyance, substantially cylindrical meaning that the cross-section of the container changes in the area of mechanical contact with the conveying units only to such a small extent that inspection of the container, e.g. of the container bottom, will not be impaired by the conveying units engaging the container. The conveying units are controllable such that successive containers can be conveyed with a predetermined spacing between them in the conveying direction along a conveying route of the conveyor arrangement.

In particular, the oppositely engaging conveying units of each pair can be moved simultaneously by means of an open-loop and/or closed-loop control unit of the conveyor arrangement along the conveying route of the throughput station such that a container located between a pair of oppositely engaging conveying units will be carried along due to the simultaneous movement of the conveying units. A simultaneous movement of the conveying units may here be realized by an arbitrary one of the embodiments of the conveying units described hereinafter and the drive system of said conveying units. In addition, the conveying route may be straight or curved, also at least partially curved, depending on the configuration and mode of transfer of the containers at and from the feed conveying device and the discharge conveying device, respectively.

Conveyance of the containers along the conveying route of the throughput station by moving simultaneously pairs of oppositely engaging conveying units allows reliable holding and guiding of the respective container, in particular also without the container resting on a conveying surface. Provided that the conveying units have a suitable structural design (see below), such reliable holding and guiding is made possible for a large number of different containers, in particular containers with different cross-sectional areas and diameters, without any changeover of the conveying units or exchange of shaped parts.

The first conveyor track and the second conveyor track may be arranged in parallel, in particular along the conveying route of the throughput station. Such a parallel arrangement is also possible for curved pieces of the conveying route by arranging the first and the second conveyor tracks at a constant distance from one another. The distance between the first and second conveyor tracks may here be predetermined on the basis of the structural design of the conveying units and the maximum diameter as well as the cross-sectional shape of the containers to be conveyed. A parallel arrangement of the first and second conveyor tracks along the conveying route guarantees here that the carried-along container will be held with a constant lateral force by the oppositely engaging conveying units throughout conveyance along the conveying route.

According to a further development, the conveying units may comprise holding devices, with oppositely engaging conveying units of a pair being oriented relative to one another in the area of the throughput station such that at least one container can be held and conveyed in a form-fit or in a force-fit manner between holding devices of opposite conveying units. The holding devices may e.g. be configured in the form of clamps, and said clamps may be configured such that they are passively or actively controllable. In particular, clamps are imaginable that are used for fixing a substantially cylindrical part of the containers in a form-fit or in a force-fit manner between clamps of oppositely engaging conveying units, the container held being supported such that it is rotatable about is longitudinal axis in the case of form-fit fixing between the clamps. This can be accomplished e.g. by providing rotatable rollers on the clamps. Said rollers may consist of a material exhibiting a sufficiently high static friction or they may be coated with such a material, so as to avoid slipping out of the conveyed containers. In addition, the holding devices may be configured in a vertically adjustable manner so as to allow an easy grade change to containers having a different height. According to the present invention, the holding devices are arranged on the conveying units of a pair such that they are disposed in opposed relationship with one another along the conveying route of the throughput station. Hence, a container to be conveyed can be fixed in position between the holding devices of such a pair and can be advanced by moving the conveying units of the pair simultaneously along the conveying route.

Holding the containers in a force-fit or in a form-fit manner by the oppositely engaging conveying units is also possible in cases where the inspection of the container makes neck handling impossible, as will be the case e.g. when the inner sidewall is inspected. In addition, the present further development allows individual containers to be taken over from an infeed flow, in which the containers are conveyed under ram pressure, i.e. in which the circumferences of the containers are in contact with one another along the conveying direction. When containers are fed under ram pressure, possible holding devices can normally not easily be introduced between the containers so as to allow holding in a form-fit or in a force-fit manner. When oppositely engaging conveying units are used, such insertion between the containers will, however, not be absolutely necessary for singling a container out of the container flow for the purpose of conveyance through the throughput station. Due to the laterally engaging holding devices and the lateral force applied thereby, a small contact area, in comparison with the total circumference of the container, will already suffice for establishing a form-fit or a force-fit hold.

The clamps of the holding devices may, for example, be configured such that they act laterally on the containers. The ends of the clamps may have provided thereon a respective support roller so that the conveyed container can deliberately be rotated by one or a plurality of friction belts acting thereon from the side, said friction belts being arranged in the area of the throughput station. The holding devices may additionally be provided with a shear mechanism of the clamps, which may have spring type characteristics so as to compensate for tolerances of the container diameter. According to the above-mentioned further developments, holding devices that are displaceable relative to the conveying unit can be advanced towards the container via a control curve and/or guidance of the conveying units along curved conveyor tracks.

The friction belt or the friction belts may be electrically driven. The drive of the friction belt(s) may be controlled via an open-loop and/or closed-loop control unit such that the container will be rotated in accordance with the container diameter so as to accomplish rotation through an angle between 70° and 110°, preferably through approximately 90°. The rotation of the container can here be accomplished by a friction belt engaging from one side or by two friction belts engaging from both sides. As has already been mentioned, the rollers of the clamps may consist of a material having a sufficiently high static friction or may be coated with such a material, e.g. rubber, so that the containers can be held in a reliable manner.

A further embodiment used for rotating the container may be realized after the fashion of a ratchet mechanism, the rollers acting on the container being provided with bearings on at least one side of the container, said bearings locking in one direction of rotation. When the linear drive is then controlled such that, during forward movement of the two conveying units acting on the container, one of the conveying units moves temporarily faster, so that there will be a difference of e.g. up to 10 mm between the clamps in the direction of movement, a rolling movement of the container through a small angle will take place due to the relative displacement of the clamps acting thereon. When, subsequently, the speed of one of the conveying units is reduced, a freewheel unit will block reverse rotation of the support rollers, so that the container will now be rotated by said angle. Subsequently, the conveying units are again at the initial position so that the process can be repeated for gradually rotating the container. Hence, a mechanism similar to a ratchet is realized for deliberately rotating the containers. It goes without saying that the locking direction of the rollers may also be provided such that the container will be rotated when the conveying units are moved apart, whereas the rollers roll on the container surface when the conveying units are again moved towards one another. The relative movement of the conveying units can here be controlled by an open-loop and/or closed-loop control unit of the conveyor arrangement.

According to a special embodiment, the holding devices may comprise one or a plurality of Y-shaped clamps, i.e. the clamps comprise an angular element which is defined by two legs and which is connected to a longitudinal element. The holding devices are arranged on the conveying units such that the opening of the angular element of the upsilon faces the container to be conveyed. Each conveying unit may comprise one or a plurality of clamps arranged one on top of the other along the longitudinal axis of the containers to be conveyed, a larger contact area with the container to be conveyed resulting in a higher reliability of conveyance due to the higher friction. The number of clamps of the conveying units of the first plurality of conveying units may differ from the number of clamps of the conveying units of the second plurality of conveying units. In particular, it is imaginable that the clamps of opposed conveying units interengage in a comblike fashion, but without any direct mechanical contact, so as to achieve holding with the highest degree of stability, which will prevent the conveyed containers from tilting. The size and shape of the Y-shaped clamps may be predetermined depending on the cross-sectional shape and size of the containers to be conveyed. The use of Y-shaped clamps has the advantage that, due to the Y-shape, a large number of cross-sectional radii can be fixed between two oppositely engaging clamps. Hence, the inspection device according to the present invention allows a product change between containers of different cross-sections, without any exchange of shaped parts for conveyance in the throughput station. Possible set-up times can thus be reduced substantially.

According to a special further development, the angle between the Y-legs of the clamps, i.e. the angle of the angular elements, can be changed especially by configuring at least the legs such that they consist of a permanently elastic material or by configuring them as angularly adjustable legs having a resilient element arranged between the legs, and/or the holding devices may be arranged on the conveying units such that they are linearly and/or angularly displaceable. A permanently elastic material is here and in the following a material which is reversibly deformable and which counteracts the deformation by means of a resetting force. By way of example, the Y-legs may consist of an elastic synthetic material, such as an elastomer, e.g. rubber or natural rubber, or they may consist of suitably shaped sheet metal or metallic webs, e.g. made of steel and e.g. in the form of a leaf spring. It follows that, by pressing the Y-legs of the clamp of the holding device onto the container to be conveyed, the angle between the Y-legs will change, depending on the respective pressure applied, so that various containers having a cross-sectional diameter within a range predetermined by the length of the Y-legs can be held in a form-fit and possibly a force-fit manner.

In order to guarantee reliable holding of the containers to be conveyed, the clamps may additionally consist of a material having a high coefficient of static friction or they may be coated with such a material on the contact side of the clamps. By way of example, elastomeric coatings may be used also in this case, said elastomeric coatings being able to adapt themselves to the shape of the container within certain limits. The materials may here be selected in accordance with the shape and the weight of the containers to be conveyed.

According to an alternative embodiment, the holding devices may be configured such that the Y-legs of the clamps enclose a right angle, i.e. they may be configured with right-angled angular elements. A right-angled angular element allows, just as an angularly adjustable angular element, conveyance of containers, in particular circular cylindrical containers, of different cross-sectional sizes. Preferably, the legs of the angular element have a length that corresponds to the radius of the maximum container to be conveyed. Possible overlapping of such legs of opposed clamps during conveyance of smaller containers can be prevented by the above-mentioned comblike formation or by vertically off-setting the respective clamps.

As has been mentioned hereinbefore, the holding devices may be arranged on the conveying units in a linearly displaceable manner. A linear displacement, in particular of the "long" Y-leg of the clamps of the holding devices, may be realized by means of suitable drive units arranged on the conveying units, such drive units being e.g. servomotors, hydraulic or pneumatic lifting cylinders, linear motors or the like, or by resiliently supporting the "long" Y-leg, said resilient support being compressed when the pairs are being formed and applying thus a resetting force to the fixed container. Preferably, the resilient supports of opposed holding devices are provided such that they have the same resilience or spring constants. Through the use of linearly displaceable holding devices, the range of conveyable container cross-sections can be extended still further. The linearly displaceable holding device additionally offers the possibility of monitoring the penetration depth of the holding devices. If the penetration depth exceeds the tolerance to be expected, it can be assumed that a container is fractured or that a bottle whose diameter is not large enough has entered the machine. In both cases, an emergency stop can be triggered immediately, which will bring the machine to a standstill preferably within less than 1 sec.

According to another further development, the holding devices may be pivotable. The pivotability is here given relative to an axis parallel to the longitudinal axis of the cylindrical containers to be conveyed. The angular elements of the clamps may e.g. be pivotably supported on the "long" Y-legs of the clamps, and a resetting element, in particular a resilient resetting element, may be provided, which resets the clamps in the empty condition to a starting position for picking up a container. The starting position may e.g. be a position at which one of the legs of the angular element defines a straight line with the "long" Y-leg. The clamps may additionally be provided with one or a plurality of locking devices that limit the pivotability of the angular elements to a predetermined angular area. By displacing the pair-forming conveying units relative to one another, as will be described in more detail hereinafter, a rotation of the conveyed containers can be caused by pivoting the holding device, said rotation positioning a container sidewall area which still is to be inspected such that it can be inspected by a sidewall inspection unit arranged on the discharge side.

According to the present invention, the first and second conveyor tracks may comprise, at least in the area of the conveying route of the throughput station, an individual drive for moving the conveying units individually and independently as well as a guide element, in particular a guide rail. In the present context, an individual drive is a drive which allows the conveying units to be moved with individual displacement-time profiles, i.e. individually and independently of one another. For guiding the conveying units along the respective conveyor track, the conveyor track according to the present further development comprises a guide element, e.g. in the form of a guide rail and/or a guide channel. Accordingly, the conveying units may comprise a complementary guide channel, a complementary guide element, e.g. a guide pin, and/or one or a plurality of suitably arranged guide rollers running, e.g. by means of a wheel flange, on the guide rail of the conveyor track. A plurality of alternative embodiments, making e.g. use of friction bearings, is here imaginable. By providing a guide rail on the conveyor track, the conveying units can be guided along the conveyor track with low friction. In addition, the conveyor track may be provided with a running surface on which respective support elements, e.g. support rollers, can roll or slide. Furthermore, the conveyor track may comprise at least one sensor for determining the position of the conveying elements along the conveyor track. In particular, a regular and periodic arrangement of sensors along at least a subsection of the conveyor track will allow to determine the position of a conveying unit on this subsection of the conveyor track. The sensor may here be configured as an optical sensor, an electrical sensor, an electromagnetic sensor or a mechanical sensor.

Tracking can especially be carried out via a control electronics for the conveying units. The respective open-loop and/or closed-loop control unit may, on the one hand, predetermine the target positions for the conveying units and, on the other hand, it may also determine and report the actual positions. The positions of the conveying units can be stored in a storage unit of the open-loop and/or closed-loop control unit. Hence, additional tracking via distance sensors or trigger light barriers can be dispensed with to a very large extent.

According to the present invention, the conveyor track and the conveying units are configured such that the conveying units can be guided individually along the conveyor track. This means that each of the conveying units comprises at least one reaction element, which, by means of electromagnetic interaction with interaction elements arranged along the conveyor track, has applied thereto a force through which the conveying unit can be accelerated and thus moved. By accurately controlling the reaction element of a specific conveying unit and/or one or a plurality of interaction elements in a limited area of the conveyor track, this application of force can be limited to a specific conveying unit, whereby the conveying unit can be conducted individually and independently of other conveying units along the conveyor track.

According to a further development, the individual drive may be a linear motor drive, the conveying units being here configured as carriages, runners, pucks, shuttles or the like, which are movable individually and independently of one another via magnetic interaction with the linear motor drive, and the conveyor arrangement comprising additionally an open-loop and/or closed-loop control unit, which is configured to move the conveying units from a pick-up site for the containers at the feed conveying device to a discharge site for the containers at the discharge conveying device.

Conveying systems having a linear motor drive are well known in the prior art. All conveying systems with a linear motor drive have in common that conveying elements or conveying units, which are specially configured for this purpose, are moved along one or a plurality of guide rails through magnetic interaction with the linear stator(s) or linear motor strings of one or a plurality of linear motors.

If a linear motor drive is used as an individual drive, the conveying units and at least the part of the respective conveyor track along the conveying route may be configured such that the conveying units can be moved in the area of the conveying route by means of a magnetic force, preferably in interaction with the conveyor track. The respective part of the conveyor track may especially be equipped with a magnetic linear drive, e.g. in the form of a synchronous or asynchronous linear motor. To this end, the respective section of the conveyor track is equipped with a plurality of electrical coils in the form of individually controllable electromagnets. In order to create a magnetic interaction between the conveying units and the individually controllable electromagnets of the conveyor track, the conveying unit may be equipped with one or a plurality of permanent magnets or non-switching electromagnets or ferrite cores.

According to an embodiment, the conveying unit may be configured as a passive conveying unit moved by interaction with the alternating electromagnetic fields generated by the individually controllable electromagnets of the conveyor track. The at least one permanent magnet or non-switching electromagnet or ferrite core of the conveying unit thus defines the above-mentioned reaction element, whereas the individually controllable electromagnets of the conveyor track define the above-mentioned interaction elements. If passive conveying units are used, the conveyor track has preferably arranged thereat a localizing unit so as to detect the position of at least one conveying unit and, preferably, of all conveying units and report it to a control of the electromagnets of the conveyor track. The localizing unit may especially be realized by the above-described sensors. The strength of the current through the electrical coils of the conveyor track may automatically be adapted by the control, depending on a power demand of the conveying unit to be moved. By individually controlling the strength of the current flowing through individual coils of the conveyor track, the conveying unit can additionally be accelerated, decelerated or moved at a predetermined constant speed.

According to an alternative embodiment, the conveying unit is, as an active conveying unit, provided with electrical coils which are capable of applying the alternating magnetic fields required for driving. Accordingly, the respective section of the conveyor track is provided with permanent magnets or non-switching electromagnets. The electric energy required for driving as well as the signals required for the purpose of control may here be transmitted to the individual conveying units via transmission by induction. Hence, the control may located off-center on the individual conveying units or it may be accommodated centrally in a separate control unit. Alternatively, the necessary electric energy may also be transmitted to the conveying units via a line arranged along the conveyor track. In addition, a combination of the conveying unit configured as an active conveying unit with a conveyor track comprising individually controllable electromagnets is imaginable.

For the use of a linear motor drive, the respective conveyor track may comprise one or a plurality of linear motor strings, which are configured as linear stators of linear motors, in particular of synchronous linear motors. According to an alternative embodiment, the linear motor strings may also be configured as asynchronous linear motors, the at least one permanent magnet and/or non-switching electromagnet of the reaction element of the conveying unit and/or an electrically conductive element of the conveying unit, e.g. in the form of a metallic plate to which the permanent magnet and/or the non-switching electromagnet is/are attached, serving here as electric conductors for the induction through the asynchronous linear motors.

In addition to the above-described part of the conveyor track within the throughput station, said conveyor track part being configured as a magnetic track, the conveyor track may additionally comprise, outside of the throughput station, at least one subsection, e.g. a feedback track, along which the conveying unit can be moved with a constant speed. To this end, the subsection may comprise a drive unit in the form of a conveyor belt, a conveyor chain or the like. By combining a conveying route having a magnetic drive within the throughput station and a feedback track with a mechanical drive, the installation costs of the conveyor arrangement in its entirety can be reduced.

According to a further development, the conveying unit may be supported on the conveyor track in a fully magnetic manner, or in a partly magnetic and partly mechanical manner, or in a fully mechanical manner. In the case of a fully magnetic support, the above-described part of the conveyor track is configured as a magnetic levitation system, electrical coils causing a magnetic levitation of the conveying unit above the conveyor track being then provided in the conveyor track and/or the conveying unit. The friction between the conveying unit and the conveyor track can thus be reduced to a minimum. In the case of a partially magnetic and a partially mechanical support, the conveying unit may additionally comprise one or a plurality of support elements, e.g. in the form of support rollers and/or guide rollers. The additional support elements roll along or slide along a running surface of the conveyor track. In the case of a fully mechanical support, the conveying unit may be supported exclusively by the above-described at least one support element. Additionally or alternatively, the support may also be of a pneumatic nature, the conveyor track being then configured as an air levitation system in the subsection in question. A pneumatic support will, just as a fully magnetic support, minimize the friction between the conveying unit and the conveyor track.

Furthermore, the conveyor arrangement may comprise an open-loop and/or closed-loop control unit, in particular a process computer, for controlling the at least one conveying unit. The open-loop and/or closed-loop control unit may here be realized by a central control unit and/or by control units arranged off-center on the conveying units. The one or the plurality of control units may be configured such that they individually control, through open-loop and/or closed-loop control, the electrical coils of the conveyor track and/or of the conveying units such that the conveying units of each pair of oppositely engaging conveying units are moved simultaneously along the conveyor track for conveying the container or the containers. The speed of the pairs can here be predetermined in accordance with a given pitch of the flow of pairs. In addition, the pairs may be accelerated or decelerated along the conveying route of the throughput station, depending on the demands on the part of the inspection units arranged in the area of the throughput station. For example, the containers may be conveyed more slowly in the area of a specific inspection unit, or they may dwell longer in this area, if, e.g. in the case of highly absorbent glass bottles, longer exposure times should be necessary or because two pictures, with different exposure times, are to be taken at the same position. By means of type management, the open-loop and/or closed-loop control unit can flexibly react to a product change by adapting the displacement-time profiles of the pairs of conveying units to the new type of containers on the basis of the parameters stored in said type management.

The individual control of the conveying units along the conveying route additionally allows precise picking up of one or of several containers from the feed conveying device, in that the holding devices of the oppositely engaging conveying units are moved towards the containers via respective curved tracks. The position and the movement of the container to be picked up may here be detected via a position sensor on the feed conveying device, such as a trigger light barrier and an incremental position encoder, and reported to the open-loop and/or closed-loop control unit of the individual drive. In the case of a plurality of containers, and also in the case of containers contacting one another in the infeed of the inspection device, one container after the other is taken hold of by a pair of conveying units in this way. This works reliably even under conditions of ram pressure. It follows that the device according to the present invention represents simultaneously a container-blocking and a container-dosing system. The use of complex elements for pressure reduction in the infeed can therefore be dispensed with, whereby installation and maintenance costs can be saved. In addition, the individual control of the conveying units allows the containers conveyed through the throughput station to be transferred precisely to the discharge conveying device. The conveying speed of the containers at the end of the conveyor track can here preferably be adapted to the continuous conveying speed of the discharge conveying device. Tilting of the containers, when the latter are put down on the discharge conveyor, can be prevented in this way.

According to another further development, the open-loop and/or closed-loop control unit may additionally be configured to move the conveying units of the first plurality of conveying units at least along part of the throughput station at a speed which is higher than that of the conveying units of the second plurality of conveying units. This results in a relative displacement of the two conveying units acting on a container, whereby the carried-along container will be rotated about its longitudinal axis, especially if the holding devices of the conveying units are configured such that they are pivotable. In particular a rotation of the carried-along container by up to 90°, preferably by approximately 90°, is imaginable, provided that the holding devices are configured in a suitable manner. In combination with the sidewall inspection units, which are referred to hereinafter and which are arranged on the infeed and on the discharge side, such a rotation can be used for fully inspecting the sidewall of the container. The rotation of the container may especially take place, as a result of the respective two conveying units moving at different speeds, when the container is taken over from the feed conveying device and/or when the container is transferred to the discharge conveying device.

According to another further development, the inspection device may additionally comprise a first inspection station arranged near the feed conveying device and configured to inspect the passing containers from the side, and/or a second inspection station arranged near the discharge conveying device and configured to inspect the passing containers from the side. The inspection stations may here especially be arranged at the end or at the beginning of the feed conveying device and the discharge conveying device, respectively. Between the two inspection stations for sidewall inspection, the containers may be rotated by means of the individual drive as described hereinbefore, so as to allow an all-around check of the containers.

According to a special further development, the first and/or second inspection station may comprise an optical system with a camera, said optical system being configured such that the side of the container to be inspected is detected within a predetermined angular area in the circumferential direction. For example, the whole container height may be illuminated with an LED area light, with one or a plurality of CCD cameras taking one or a plurality of pictures of the container sidewall from different angles of view. For example, two pictures of the sidewall can be taken from different angles of view via a camera and an optical system comprising four mirrors, the angles of view deviating from one another e.g. by 90° in the circumferential direction. In the case of transparent objects, the sidewall inspection station inspects not only the sidewall located between the container axis and the recording direction but also the sidewall located on the other side of the container axis. It follows that, by detecting a respective 90° angular area on the front and on the rear side of the container, an all-around detection of the sidewall can be carried out, by rotating the container by 90° in the throughput station, with the inspection stations arranged on the infeed and on the discharge side.

In particular, the detected angular area of the first inspection station may be smaller than the angular area of the second inspection station. The detected angular area of the first inspection station may e.g. be an area between 40° and 60°, whereas the detected angular area of the second inspection station will accordingly be larger than 90°. Hence, also containers fed under ram pressure conditions can be inspected with respect to their sidewalls in the feed conveying device. The optical systems of the first and second inspection stations, in particular possible optical elements and mirror elements, respectively, may be automatically adjustable so that they can be adapted to the dimensions of a new container in the case of grade changes.

According to another further development, the inspection device may further comprise a bottom inspection station in the area of the throughput station, said bottom inspection station being configured to inspect the bottoms of the passing containers. Such a bottom inspection station may e.g. comprise a camera, which will take a picture of the container bottom that is uniformly illuminated by an LED flash lamp. To this end, the bottom of the container must be freely accessible, in that the container is conveyed in a suspended condition, in the area of the inspection station. The sensor data or optical data recorded by the inspection stations may be transmitted to an evaluation unit, e.g. a computing unit, of the inspection device, which will evaluate the data automatically so as to detect damage or contamination. The data may be transmitted in a wire-bound or in a wireless fashion.

The above-mentioned objects are also achieved by a method of continuously inspecting containers, in particular bottles, said method comprising the following steps: successive feeding of containers to a throughput station of an inspection device, conveying the fed containers in the throughput station, inspecting the fed containers in the throughput station and discharging the inspected containers, the fed containers being conveyed in the throughput station by means of a conveyor arrangement comprising an individual drive and a plurality of conveying units movable individually and independently of one another by means of the individual drive.

The same variations and further developments which have been described hereinbefore in connection with the inspection device according to the present invention are also applicable to the continuous inspection method. In particular, the containers of the throughput station can be fed by means of a feed conveying device as a flow of containers. The fed containers are taken up by the conveyor arrangement individually or in the form of a pack and they are conveyed along a conveying route of the throughput station by means of the individual drive and the plurality of conveying units independently of one another and in an individually controllable manner. Inspection of the fed containers in the throughput station can be carried out by one or a plurality of the above-described inspection stations.

According to a further development, the fed containers can be conveyed in the throughput station by means of oppositely engaging conveying units, the individual drive being a linear motor drive and the conveying units being configured as carriages, which are movable in a controlled manner through magnetic interaction with the linear motor drive. Also in this case, the above-described further developments are applicable. In particular, a first plurality of conveying units can be moved along a first conveyor track of the conveyor arrangement and a second plurality of conveying units can be moved along a second conveyor track of the conveyor arrangement such that, for taking over a container from the feed conveying device, a pair of oppositely engaging conveying units is established, which is subsequently de-established for transferring the container to the discharge conveying device. By means of an open-loop and/or closed-loop control unit, the respective conveying units of the pairs can be moved simultaneously along the conveying route. A rotation of the container can be caused by moving the conveying units at different speeds when the container is taken over and when it is transferred or moved along part of the conveying route. An all-around check of the container sidewall can thus be executed through sidewall inspection stations arranged on the infeed and on the discharge side.

According to a special further development, the containers can be fed to the conveyor arrangement of the throughput station in a mutually abutting mode, i.e. under pressure. In this case, the open-loop and/or closed-loop control unit controls the movement of the oppositely engaging conveying units such that a blocking and dosing function is realized through the precise formation of pairs when the containers are taken over. The use of complex devices for reducing the pressure in the infeed can therefore be dispensed with.

The inspection device described needs less installation space in a system for empties inspection, since containers can be moved into the device under ram pressure as well as separately of one another and since the pressure reduction unit is therefore no longer necessary. Making use of the individual drive, a defined distance between the containers is established at the discharge of the throughput station, independently of the infeed distance. This allows the use of sidewall inspection units having a viewing angle range of more than 90° on the discharge side and/or a discharge of the inspected containers in a segment-type discharge process. Since the containers are held in a form-fit or force-fit manner while passing through the throughput station, the degree of tilting will be small so that inspection units which are sensitive in this respect can operate in the best possible way. The drives including torque transmission of the normally used belt station are replaced by the linear motor drive, which can react more flexibly to grade changes. For the purpose of cleaning or servicing, the conveying units can be moved, individually or in common, out of the throughput station and into a servicing station that is specially provided for this purpose.

In addition, other than in the case of known belt drives, the routing in the throughput station may deviate from a linear routing, since the independent control of the conveying units will easily allow also movements along a curved track. The conveying route of the throughput station can thus be configured as a 90° to 180° curve so as to reduce the length of the process route. In order to prevent a plurality of inspection stations from mutually influencing one another in the area of the throughput station, said inspection stations should normally be prevented from triggering simultaneously and causing e.g. a flash illumination. Due to the possibility of moving the containers within the throughput station by means of the individual drive such that a defined distance is established therebetween, this can easily be excluded. It follows that the described devices and methods will allow simplified plant construction and they will render the inspection device more flexible with respect to the container types to be inspected. Set-up times can thus be reduced and the use of complex elements can be rendered superfluous.

Additional features and exemplary embodiments as well as advantages of the present invention will be explained hereinafter in more detail making reference to the drawings. It goes without saying that the embodiments do not exhaust the scope of the present invention. It also goes without saying that some or all of the features described hereinafter may also be combined with one another in other ways.

DETAILED DESCRIPTION

Figure 1:
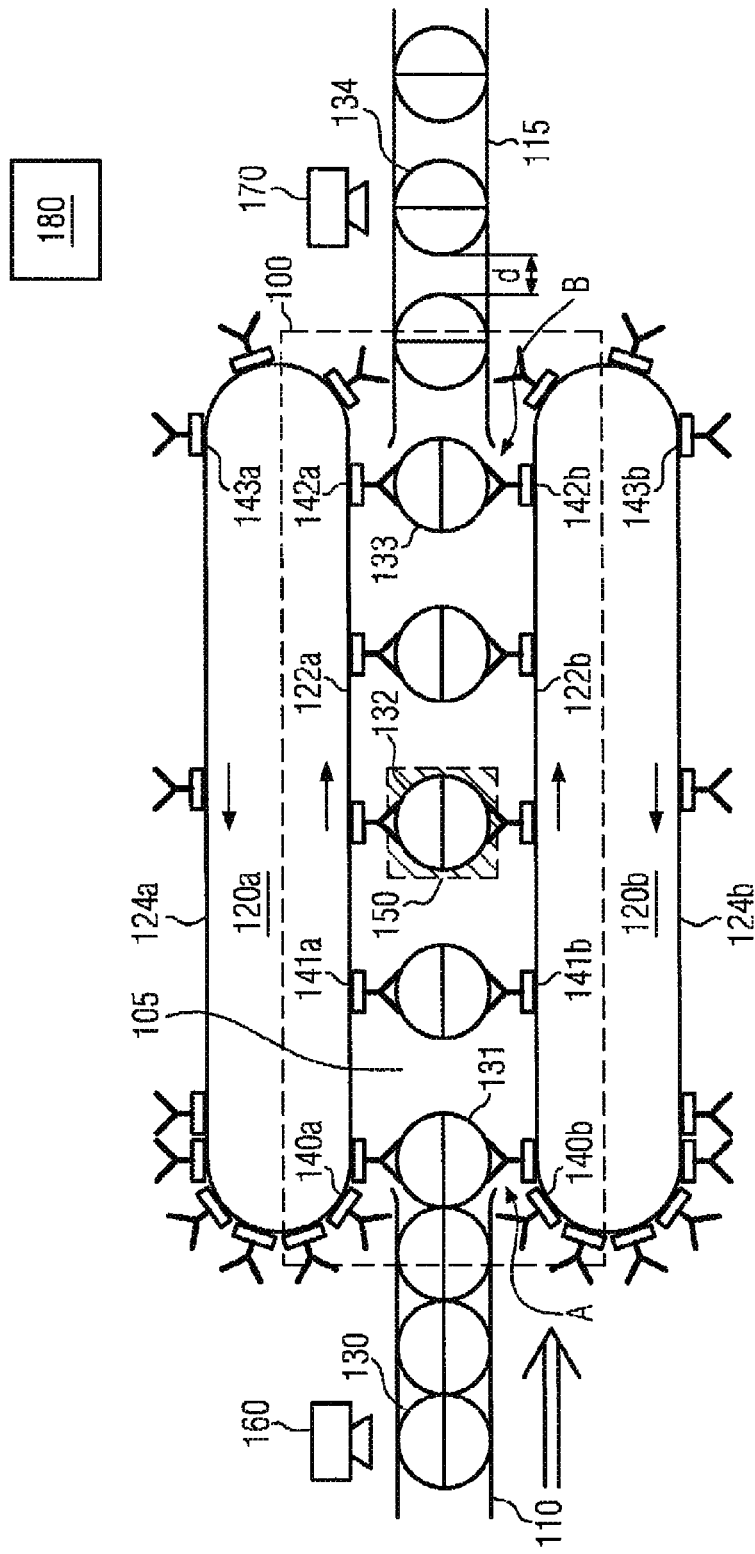
FIG. 1 shows schematically an exemplary embodiment of an inspection device according to the present invention in a top view.

In the figures described hereinafter, like reference numerals identify like elements. For reasons of clarity, like elements will only be described when they appear for the first time. However, it goes without saying that the variants and embodiments of an element described with respect to one of the figures may also be applied to the corresponding elements in the other figures.

FIG. 1 shows a schematically an exemplary embodiment of an inspection device according to the present invention in a top view. In addition to a feed conveying device 110 used for feeding containers 130 in succession and a discharge conveying device 115 used for discharging the inspected containers 134, the inspection device shown comprises a throughput station 100 arranged between the feed conveying device and the discharge conveying device and represented here by a broken line. According to the present invention, the throughput station 100 comprises a conveyor arrangement with an individual drive and a plurality of conveying units 140a to 143a and 140b to 143b, which are movable by means of the individual drive individually and independently of one another and which convey the containers along a conveying route 105 of the throughput station 100 from the feed conveying device to the discharge conveying device. To this end, the conveyor arrangement comprises a first conveyor track 120a and a second conveyor track 120b having each a plurality of conveying units 140a to 143a and 140b to 143b, respectively, arranged therealong. The closed conveyor tracks 120a and 120b shown here each consist of a subsection 122a and 122b, respectively, arranged along the conveying route 105 within the throughput station 100, and of a feedback track 124a and 124b, respectively, along which the unladen conveying units are returned for picking up a new container at the pick-up site A.

The conveyor tracks are here arranged relative to one another and relative to the feed conveying device 110 and the discharge conveying device 115 such that, in the area of the throughput station, pairs of oppositely engaging conveying units for the containers can be formed, each of said pairs comprising a conveying unit of the first plurality of conveying units and a conveying unit of the second plurality of conveying units. To this end, the conveyor tracks comprise curved pieces in the area of the pick-up site A, the conveying units 140a and 140b moved along these curved pieces approaching one another until their Y-shaped holding devices receive between them a container 131 from the flow of containers 130 of the feed conveying device 110 in a form-fit or in a force-fit manner. Due to the special shape of the holding devices, this precise picking up of a single container 131 can reliably be carried out, even if the containers 130 are fed under pressure, i.e. in a mutually abutting mode. The container 131 fixed between the holding devices of the oppositely engaging conveying units can here be lifted from the feed conveying device 110 so that, while the container is being conveyed along the conveying route 105, the bottom area as well as the outlet area of the conveyed container are freely accessible.

According to the further development shown here, the first and second conveyor tracks 122a and 122b are arranged parallel to one another along the conveying route 105, so that, during the entire conveyance along the conveying route, the conveyed containers 131 to 133 are reliably held and conveyed by the pairs defined. Exemplarily, a bottom inspection station 150 is schematically shown at the conveying route 105 shown here, said bottom inspection station 150 recording, e.g. by means of a CCD camera, an optical picture of the bottom of the container 132 illuminated by an LED flash lamp. The data of this inspection station can be transmitted to the processing unit 180, which is here schematically shown, for further processing. The processing unit 180 evaluates the data automatically, so as to detect e.g. damage of the container bottom. It goes without saying that additional inspection units, which are not shown here, may be arranged in the area of the throughput station 100 for inspecting the conveyed containers.

At the end of the conveying route 105 of the throughput station 100, the pairs of conveying units 142a and 142b are de-established at a discharge site B, e.g. by diverging curved pieces of the conveyor tracks 120a and 120b, so that the carried-along container 133 is transferred to the discharge conveying device 115. Since the conveying units are moved along the conveyor tracks 122a and 122b individually and independently of one another by means of an individual drive according to the present invention, the containers conveyed in the throughput station 100 can be conveyed, in a particular in a precise manner and at a desired distance from one another. This also allows to adjust a desired pitch d of the outgoing flow of containers 134 after the inspected containers have been transferred to the discharge conveying device 115. This arrangement can be used in a particularly advantageous manner, since this system allows to use also discharge systems that are not able to discharge closely packed containers in an upright condition. Also for closely packed containers, the discharge rate is positively influenced by purposefully creating a distance. In order to avoid here a back-up situation, the speed of the discharge conveyor may be increased by the magnitude of the distance from one container to the next in the infeed plus a desired gap.

It follows that the inspection device shown allows the containers 130 to be fed under pressure as well as to move the conveyed containers apart to a desired discharge pitch d. The movement of the conveying units along the conveying route 105 takes here place with an individual displacement-time profile via an open-loop and/or closed-loop control unit of the conveyor arrangement, which may e.g. be configured as part of the processing unit 180. According to the further development shown here, the conveyor tracks 120a and 120b are provided throughout their length with an individual drive, e.g. in the form of the linear motor drive shown in FIG. 2, so that the conveying units can also be returned along the feedback tracks 124a and 124b with an individual displacement-time profile. In particular, the conveying units can be guided along the feedback tracks at a higher speed so as to keep the total number of necessary conveying units small. Moreover, the feedback tracks 124a and 124b can be used for buffering conveying units. As has already been described, also feedback tracks having a continuous drive, e.g. in the form of a belt conveyor or a conveyor chain, may be provided for reducing the costs of installation and operation.

According to the further development shown here, the inspection device additionally comprises a first sidewall inspection station 160 arranged on the infeed side at the feed conveying device 110 and used for inspecting a first angular area of the sidewalls of incoming containers 130, and a second sidewall inspection station 170 arranged at the discharge conveying device 115 and used for inspecting a second angular area of the sidewalls of outgoing containers 134. As indicated in FIG. 1 by the container dividing line, the containers may be rotated by e.g. 90° while they are being conveyed, so that the first and second sidewall inspection stations 160 and 170 will inspect respective other subareas of the sidewalls of the containers so as to allow an all-around check of the container sidewall. According to the schematic further development shown here, the containers 133 are rotated by 90° when they are transferred to the discharge conveying device 115. Since the incoming containers 130 according to this further development are conveyed in a mutually abutting mode, the angular area detected by the first sidewall inspection station 160 is normally smaller than 90°. Since the flow of containers is, however, moved apart to a pitch din the discharge conveying device 115, the second sidewall inspection station 170 will be able to detect also an angular area larger than 90°, so that, in combination with the area detected by the first sidewall inspection station 160, a complete detection of the sidewalls of the conveyed containers will be obtained. Also in this case, the acquired sensor and/or image data of the sidewall inspection stations 160 and 170 can be transmitted to the processing unit 180 for automatic further processing. The variant shown here, in the case of which the conveyed containers are rotated during transfer to the discharge conveying device 115, only represents one possible variant. Alternatively, the containers may be rotated when they are taken over from the feed conveying device 110 or they may be rotated by a respective smaller angle when they are taken over as well as when they are transferred. Furthermore, an at least partial rotation of the containers by an angle smaller than 90° can also be accomplished by moving the conveying units 141a and 141b of each pair at different speeds. Two special further developments for rotating the conveyed containers will be explained hereinafter in detail in connection with FIG. 3A, FIG. 3B, FIG. 3C, FIGS. 3D and 4.

Figure 2:
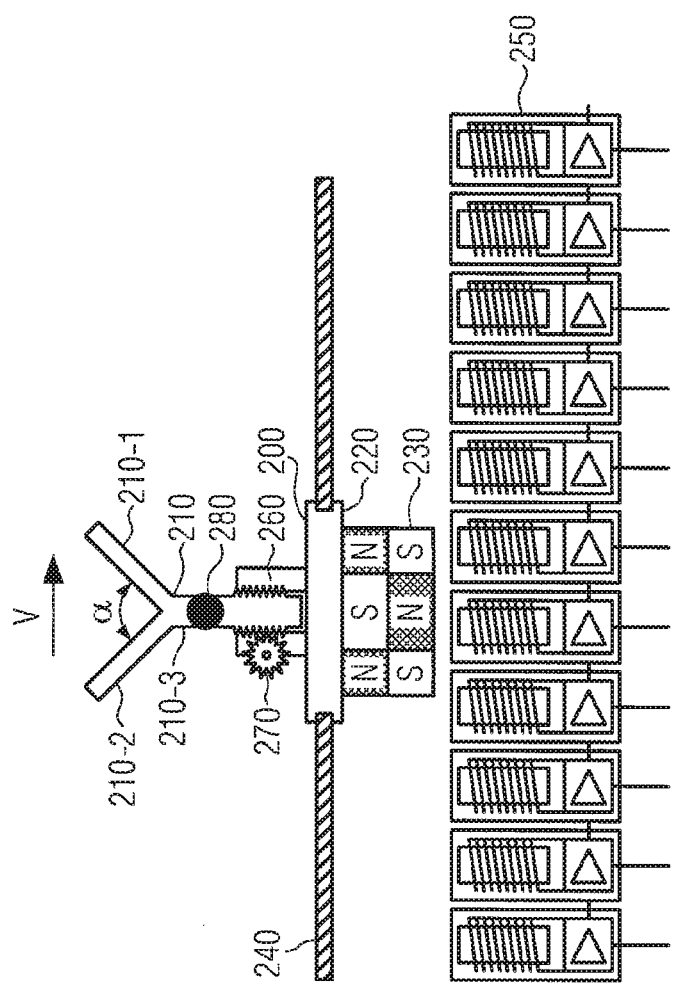
FIG. 2 shows an exemplary embodiment of a conveying unit and a conveyor track with a linear motor drive.
Figure 3:
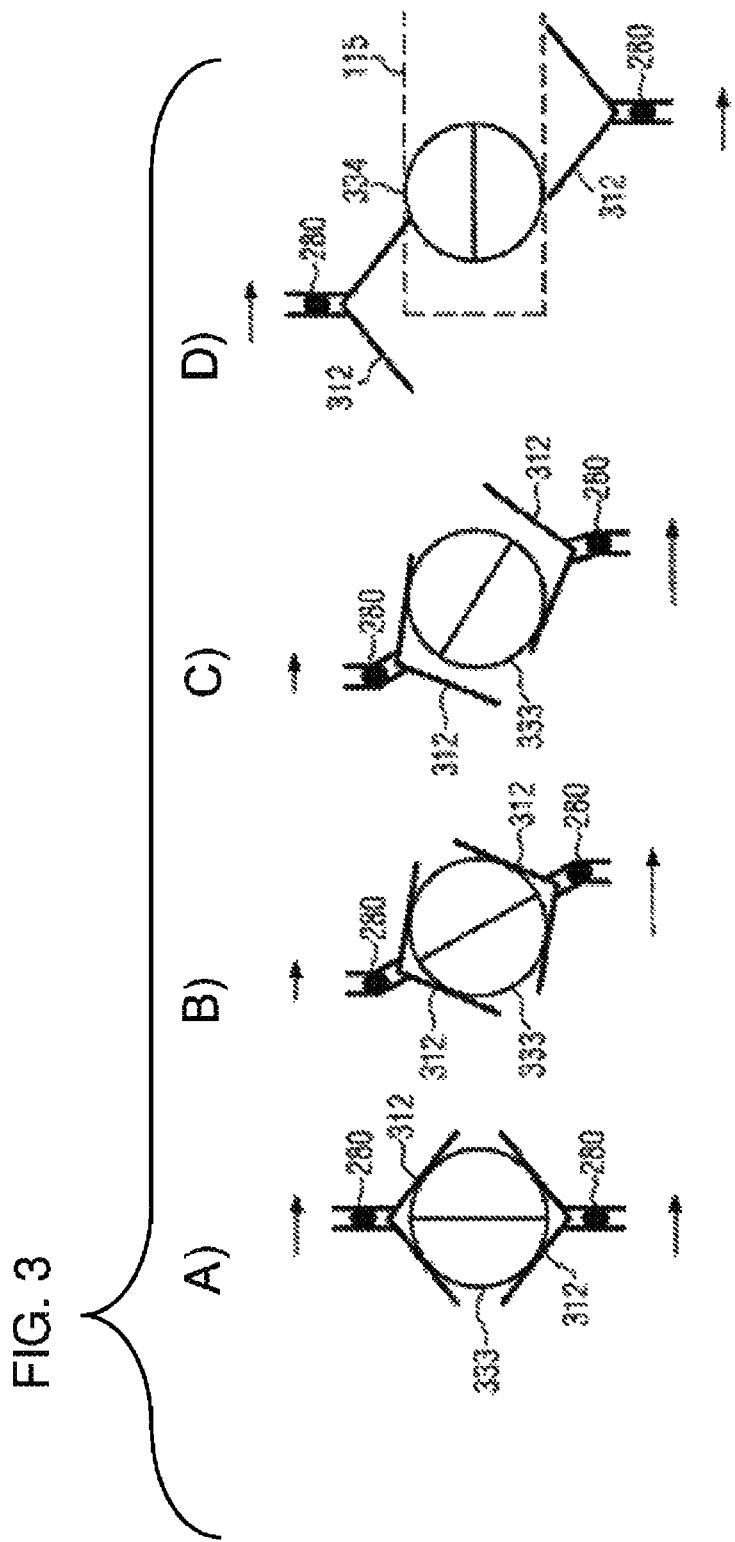
FIG. 3A, FIG. 3B, FIG. 3C, FIG. 3D show schematically the rotation of a container by 90° in the discharge of the throughput station according to the present invention.

FIG. 2 shows an exemplary embodiment of a conveying unit and a conveyor track in cases where a linear motor drive is used for individually moving the conveying unit. The present invention is, however, not limited to the special embodiment of the conveying unit shown here, but it is applicable to any kind of individually movable conveying units as long as oppositely engaging conveying units are able to move the containers along the conveying route in a form-fit or in a force-fit manner. The conveying unit 200 shown here can be guided along the conveyor track by means of a guide rail 240. According to this special embodiment, the conveying unit is supported on the guide rail 240 by a friction bearing 220. The figure additionally shows a holding device 210 by means of which the conveying unit will be able to take hold of and convey the containers.

According to the exemplary embodiment shown here, the holding device 210 is depicted in the form of an upsilon which is open towards the container and which has an opening angle α between the two "short" Y-legs 210-1 and 210-2. The "long" leg 210-3 of the Y is fixed via a holder 260 to the conveying unit 200 in a linearly displaceable manner, a gear 270, which is driven by a servomotor (not shown), meshing with a toothed rack of the "long" Y-leg 210-3. As regards the lateral displacement of the holding device 210, a large number of alternative embodiments is imaginable. For example, the holding device 210 may be fixed to the conveying unit 200 by means of a resilient element such that, for receiving the container to be conveyed, the clamp defined by the Y-legs 210-1 and 210-2 is linearly displaceable relative to the friction bearing 220 by compressing this resilient element.

The sides of the Y-legs 210-1 and 210-2 of the clamp facing the container may be coated with an adherent layer so as to guarantee reliable holding of the container when the latter is conveyed in a suspended condition. Alternatively, the whole legs 210-1 and 210-2 may consist of this material having a sufficiently high static friction, and, in particular, the Y-legs may be made of a resiliently deformable material. In the latter case, the angle between the two Y-legs may be adapted to be changed, by deforming the resilient material, such that the clamp will be able to reliably receive therein a large number of different container types with different cross-sectional diameters.

According to the special further development shown here, the Y-shaped clamp 210 is additionally supported on the conveying unit 200 such that it is pivotable via a pivot bearing 280. Resetting elements, which are here not shown and which are used for resetting the unladen clamp 210 to a predetermined starting position, may be provided. Moreover, a pivotal movement of the clamp may be limited to a desired angular area by locking devices, which are here not shown.

The drive of the passive conveying unit shown here is effected by magnetic interaction between the reaction element 230 of the conveying unit and a plurality of electrical coils 250 along the conveyor track. The electrical coils 250 can be controlled individually by means of an open-loop and/or closed-loop control unit (not shown) and, as electromagnets, they can individually undergo a polarity reversal. Due to interaction of the magnetic fields of the electromagnets with the here shown permanent magnet of the conveying unit, the conveying unit is subjected to an action of force which, on the basis of a suitable control of the electromagnets 250, results in an acceleration, a deceleration or a constant movement of the conveying unit along the guide rail 240. The here shown reaction element 230 of the conveying unit consists of three permanent magnets arranged in an alternating mode and perpendicular to the guide rail, the width of the central permanent magnet corresponding approximately to the distance between two neighboring electrical coils of the conveyor track and the width of each of the outer permanent magnets corresponding approximately to half the distance between the neighboring electrical coils. It follows that, in the case of an alternating polarization of neighboring electromagnets in the conveyor track, a maximum force can act on the reaction element along the guide rail. By individually controlling the electromagnets 250, the conveying unit 200 can be moved along the guide rail 240 at the speed V predetermined by an open-loop and/or closed-loop control unit of the conveyor arrangement. In particular, a large number of conveying units can be moved along the guide rails in a controlled manner such that an adaptation of the container pitch along the conveying route will be effected (see above).

FIG. 3A, FIG. 3B, FIG. 3C, FIG. 3D show schematically the rotation of a container by 90° in the discharge of the throughput station according to the present invention. In said figure, the conveyed container 333 is shown in four different phases a) to d) of this rotation. It goes without saying that the further development shown is only of an illustrative nature and does not limit the scope of the present invention. As regards the conveying units, only the clamps 312 thereof are shown in said figure, said clamps 312 being supported on the conveying units via pivot bearings 280.

On the basis of the pivot bearings 280, the clamps 312 can be pivoted by moving the pair-forming conveying units at different speeds, as indicated in the present case by the different lengths of the motion arrows. By moving the two conveying units of a pair at different speeds along their conveyor tracks, the clamps 312 of said conveying units move increasingly away from one another, thus causing a rotation of the carried-along container 333, as indicated here by the longitudinal line.

At the beginning of this development (cf. subfigure a)), the opposed conveying units of the pair move at the same speed, so that the fixed container 333 is symmetrically held between the opposed clamps 312. In comparison with the situation in subfigure a), the lower conveying unit has been accelerated in subfigure b), so that the associated clamp 312 will move ahead of the clamp of the upper conveying unit. This has the effect that both clamps 312 are simultaneously pivoted about the respective pivot bearing 280, whereby the carried-along container 333 is partially rotated. In subfigure c), the two conveying units have already been moved away from one another to such an extent that the carried-along container 333 is no longer in contact with a respective one of the legs of the clamps 312. Due to the static friction between the container 333 and the other leg, the container will, during the increasing degree of shearing of the two clamps, roll on the legs such that the initial rotation of the container will be continued until a rotation by approximately 90° has been reached.

Subfigure d) shows the situation after the end of the rotation of the container 334. The latter has already been put down on the discharge conveying device 115. Due to the resetting elements, which are not shown, the clamps 312 are pivoted back to their original position when the container 334 has been put down, so that the conveying units are prepared to pick up another container. The container 334, which has now been rotated, can be inspected in a downstream sidewall inspection station with respect to the hitherto unexamined sidewall area.

Figure 4:
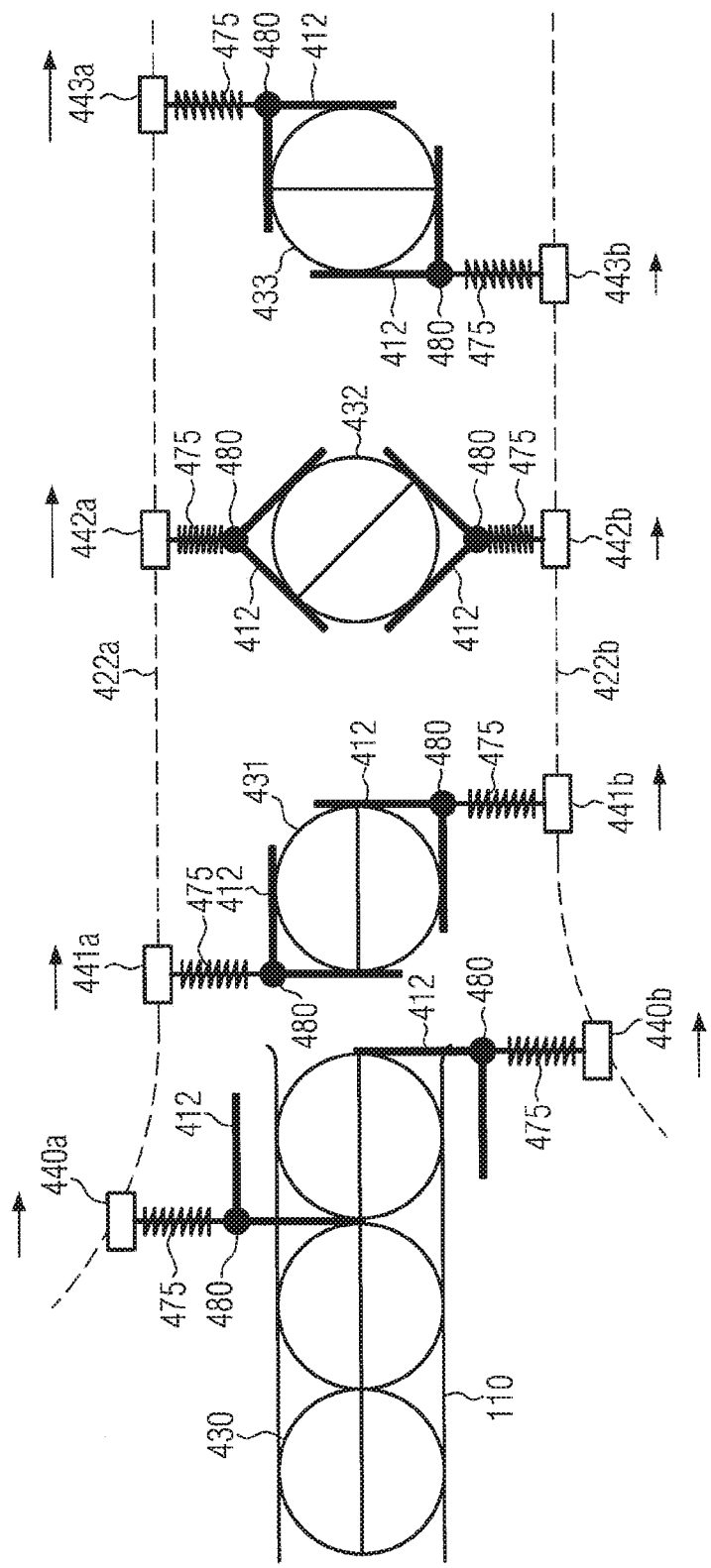
FIG. 4 shows schematically the rotation of a container by 90° in the infeed of the throughput station according to the present invention.

FIG. 4 shows schematically an alternative further development in the case of which a container is rotated by 90° in the infeed of the throughput station. According to the further development shown here, the incoming containers 430 are fed under pressure, i.e. in a mutually abutting mode, by means of the feed conveying device 110. Also according to this further development, each of the conveying units 440*a* to 443*a* and 440*b* to 443*b*, respectively, is provided with a clamp 412 which is supported on the respective conveying unit by means of a pivot bearing 480. In addition, the holding devices of the conveying units shown here are supported by means of a resilient element 475, so that the clamp 412 is linearly displaceable with respect to the support of the conveying unit on the respective conveyor track 422*a* or 422*b*.

Figure 5:
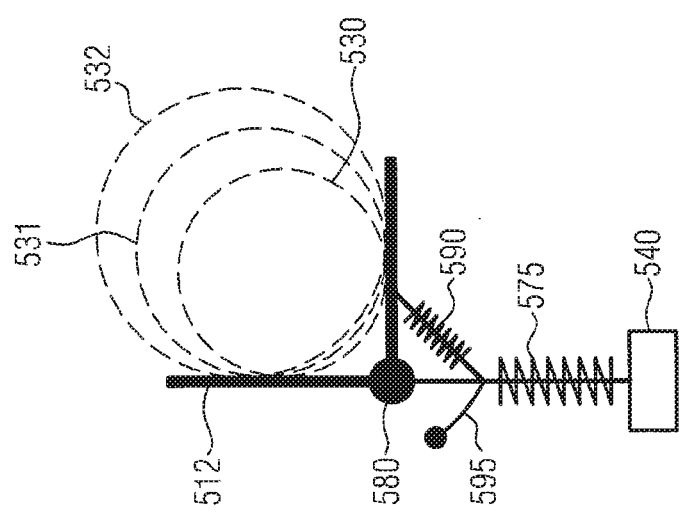
FIG. 5 shows an exemplary further development of a holding device for containers of different diameters according to the present invention.

Other than in FIG. 3A, FIG. 3B, FIG. 3C, FIG. 3D, the initial position of the clamps 412 of the holding devices shown in FIG. 4 is, e.g. by a resetting element that is not shown, predetermined such that a Y-leg of the clamp is aligned along a straight line with the linearly displaceable leg of the holding device. The clamps 412 of opposed conveying units 440*a* and 440*b* are again arranged relative to one another such that their openings are located in opposed relationship with one another. According to the further development shown here, the Y-legs of the clamps 412 are exemplarily configured with right angles and rigidly, so that, as shown in FIG. 5, a large number of containers with different container diameters can be held reliably. The Y-leg arranged in linear alignment with the "long" leg of the holding device of the conveying unit 440*a* can, provided that the Y-leg is configured in a suitable manner and that the curved piece of the conveyor track 422*a* is arranged in a suitable manner, be inserted into the infeed flow between the container to be picked up and the downstream container in said flow. Simultaneously, the conveying unit 440*b* approaches the feed conveying device 110 along a respective curved piece of the conveyor track 422*b* such that the Y-leg 412 arranged upstream of the container to be picked up will serve as a blocking means preventing the container from slipping out of the transfer site. A single container can thus be accurately taken over from the flow of containers 430, and a dosing and blocking function is simultaneously fulfilled by the formation of the pair of conveying units 440*a* and 440*b*.

The conveying units 441*a* and 441*b* are moved towards each other to such an extent that, according to this further development, both Y-legs of the respective clamp 412 are moved into contact with the container 431 to be held. In the course of this process, the resilient elements 475 may be compressed at least partially so that the Y-legs of the clamps 412 abutting in a direction laterally to the conveying direction will be pressed with sufficient force against the container wall of the container 431. The dimensions of the Y-legs in the longitudinal direction of the containers can here be chosen such that the static friction prevailing between the clamps 412 and the outer surface of the container will be sufficiently high for reliably holding the conveyed container 431. Also when the container is rotated while it is taken over from the feed conveying device 110, this rotation will take place by moving the pair-forming conveying units 442*a* and 442*b* at different speeds, as indicated by the arrows of different lengths in the present figure. In this case the conveying unit 442*a* is moved by means of the open-loop and/or closed-loop control unit at a speed that is higher than that of the conveying unit 442*b* so that the carried-along container 432 will be rotated clockwise, as indicated by the longitudinal line of said container. In the course of this process, the clamps 412 are pivoted about the pivot bearing 480 such that both Y-legs of the clamps will always remain in contact with the container. In view of the fact that this, however, leads to a change in the distance of the respective pivot bearing 480 from the conveying units 442*a* and 440*b*, respectively, the resilient elements 475 will be compressed by these changes in distance.

By continuing to move the conveying unit 443*a* at a higher speed than the conveying unit 443*b*, this rotation of the container 433 will continue until a rotation of about 90° has taken place. In this situation, the position of the clamps 412 has changed by 90° relative to their initial position, both Y-legs of each clamp being still in contact with the outer surface of the container. For further conveyance of the container 433, the pair-forming conveying units 443*a* and 443*b* can then be moved on at the same speed. After transfer of the carried-along container to the discharge conveying device, the respective clamps 412 can be returned to their original positions by a suitably provided resetting element, so as to pick up a further container of the infeed flow 430. A large number of alternative further developments for accurately picking up and reliably conveying a container as well as for rotating the container by moving, at different speeds, the conveying units of the pair holding the container is imaginable.

FIG. 5 shows an exemplary further development of a holding device for containers having different diameters according to the present invention. As has already been the case in FIG. 4, also the Y-legs of the clamp 512 according to this further development are provided at right angles and are supported at their point of intersection via a pivot bearing 580 on a part of the holding device, which is linearly displaceable by means of a resilient element 575, on the here schematically shown bearing 540 of the conveying unit. Representatively, three exemplary container cross-sections 530, 531, and 532 are shown in this figure by a broken line, both Y-legs of the clamp 512 being always in contact with the outer surface of the container. For containers 530 whose diameter is smaller than the length of the Y-legs of the clamp 512, the oppositely engaging clamps of the respective conveying units can be arranged in an offset mode along the pivot axis of the pivot bearing 580 and, consequently, along the longitudinal axis of the container, as shown e.g. in FIG. 6.

According to the further development shown here, the holding device is additionally provided with a resilient resetting element 590 which returns the clamp 512 to the here shown starting position in the unladen condition. In addition, a locking device 595, e.g. in the form of a locking pin, may be provided, which limits the pivotal movement of the clamp 512 to a desired angular area. The carried-along container can thus be prevented from slipping out of the oppositely engaging clamps of the pair of conveying units.

Figure 6:
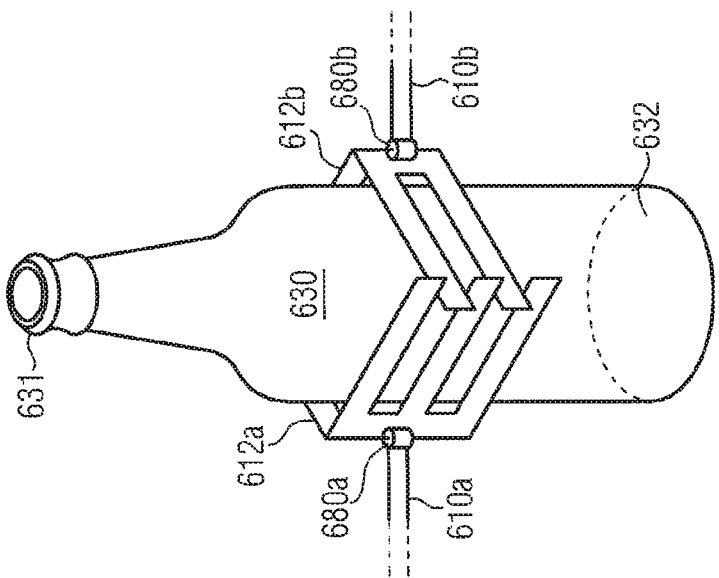
FIG. 6 shows schematically the interengagement of oppositely engaging clamps of holding devices according to the present invention.

FIG. 6 shows schematically the interengagment of oppositely engaging clamps of holding devices according to a special further development. According to this exemplary further development, the holding devices of the oppositely engaging conveying units are provided with a plurality of clamps 612*a* and 612*b*, which are arranged in an offset mode along the pivot axis and which interengage in a comblike manner in the non-limiting further development shown here. For example, the holding device of the conveying units of the first plurality may comprise three clamps 612*a* offset along the longitudinal axis of the container and jointly supported via a pivot bearing 680*a* on the "long" leg 610*a* of the holding device. In a corresponding manner, the holding device of the conveying unit of the second plurality of conveying units may be provided with two clamps 612*b* offset along the longitudinal axis of the container and supported via a corresponding pivot bearing 680*b* on the "long" leg 610*b* of the holding device. In the embodiment shown, the clamps of the two holding devices interengage, without impeding one another, due to their length which is large in comparison with the diameter of the container 630. Due to the comblike interengagement of the clamps, the container is here reliably prevented from tilting while it is being conveyed along the throughput station.

FIG. 6 shows exemplarily a bottle 630, which is held in a suspended condition between the clamps 612*a* and 612*b*, so that the container bottom 632 and the outlet area 631 of the bottle are simultaneously freely accessible. Hence, the whole bottle 630 can be inspected along its longitudinal direction by means of suitable inspection units, so that both the bottom area 632 and the outlet area 631 can be inspected for damage and contamination.

Figure 7:
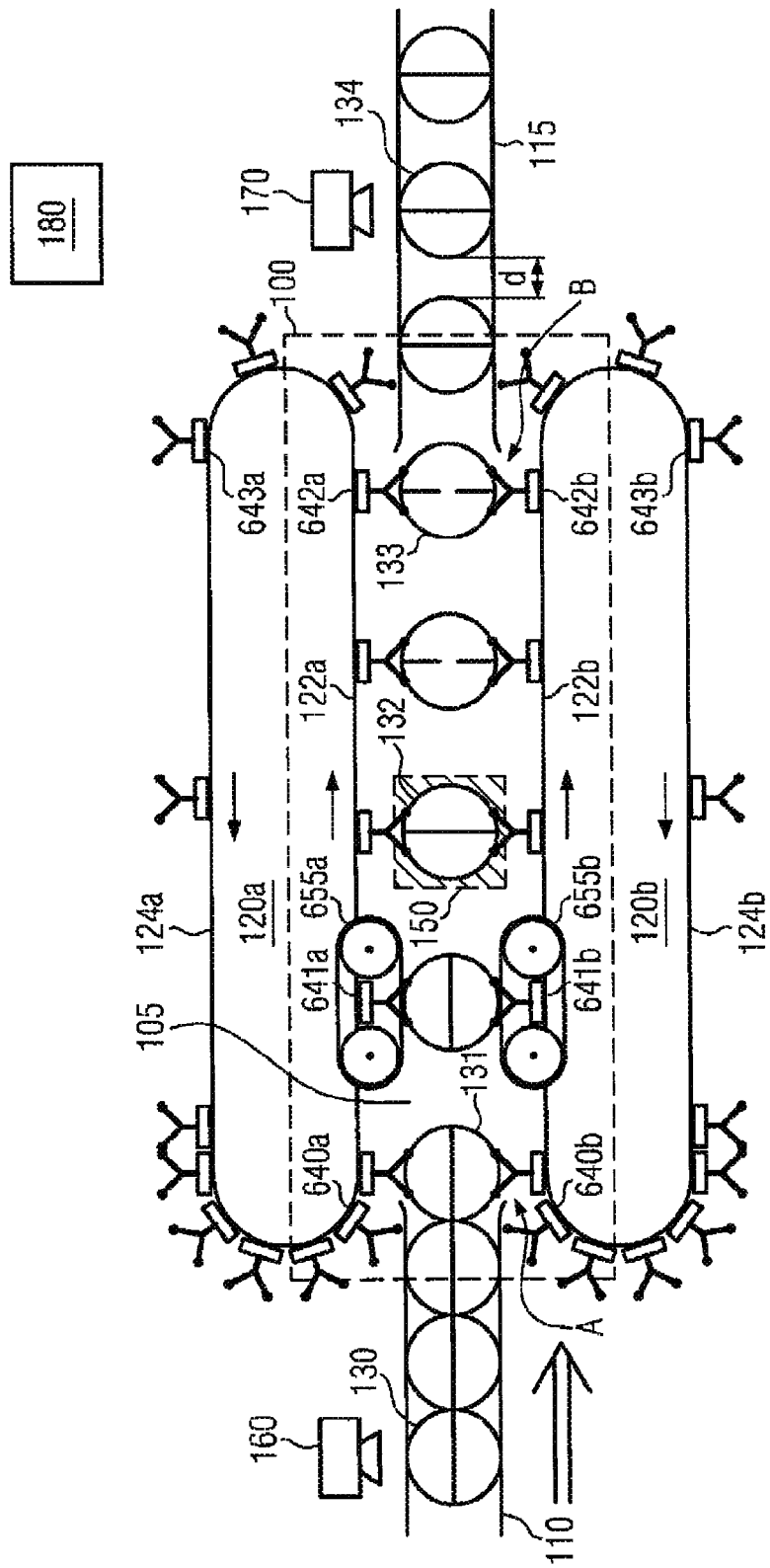
FIG. 7 shows a variation of the further development according to FIG. 1 with end-mounted rollers on the clamps of the holding devices.

FIG. 7 shows a variation of the further development according to FIG. 1 with end-mounted rollers on the clamps of the holding devices. The inspection device shown corresponds substantially to the further development according to FIG. 1 and will therefore not be described once more. In addition, the holding devices of the conveying units 640*a* to 643*a* and 640*b* to 643*b* according to the further development of FIG. 7 are formed with end-mounted rollers provided on the clamps and holding the conveyed containers in a form-fit manner such that the latter are prevented from slipping out on the one hand and adapted to be rotated about their longitudinal axis on the other. The rollers may especially consist of a material exhibiting a sufficiently high static friction or they may be coated with such a material, so as to avoid slipping out of the conveyed containers. For rotating the containers fixed between the rollers of opposed holding devices, two friction belts 655*a* and 655*b* are provided in the non-limiting further development shown here, said friction belts being arranged on either side of the conveying route 105 such that the rollers of the conveying units 641*a* and 641*b* can be brought into mechanical engagement therewith. Due to the movement of the container, which is held by the conveying units, relative to the friction belts and/or a friction belt rotation that is driven in a controlled manner, the containers can be rotated by a desired angle indirectly via the rollers of the holding devices. The open-loop and/or closed-loop control unit 180 can drive the friction belts 655*a* and 655*b* such that containers of different diameters will be rotated by the desired angle. It goes without saying that also further developments comprising only one friction belt 655*a* or 655*b*, which engages from one side, are possible. Furthermore, the friction belts 655*a* and 655*b* may be configured such that they can be displaced to the side so as to allow a grade change to containers having different diameters.

Figure 8:
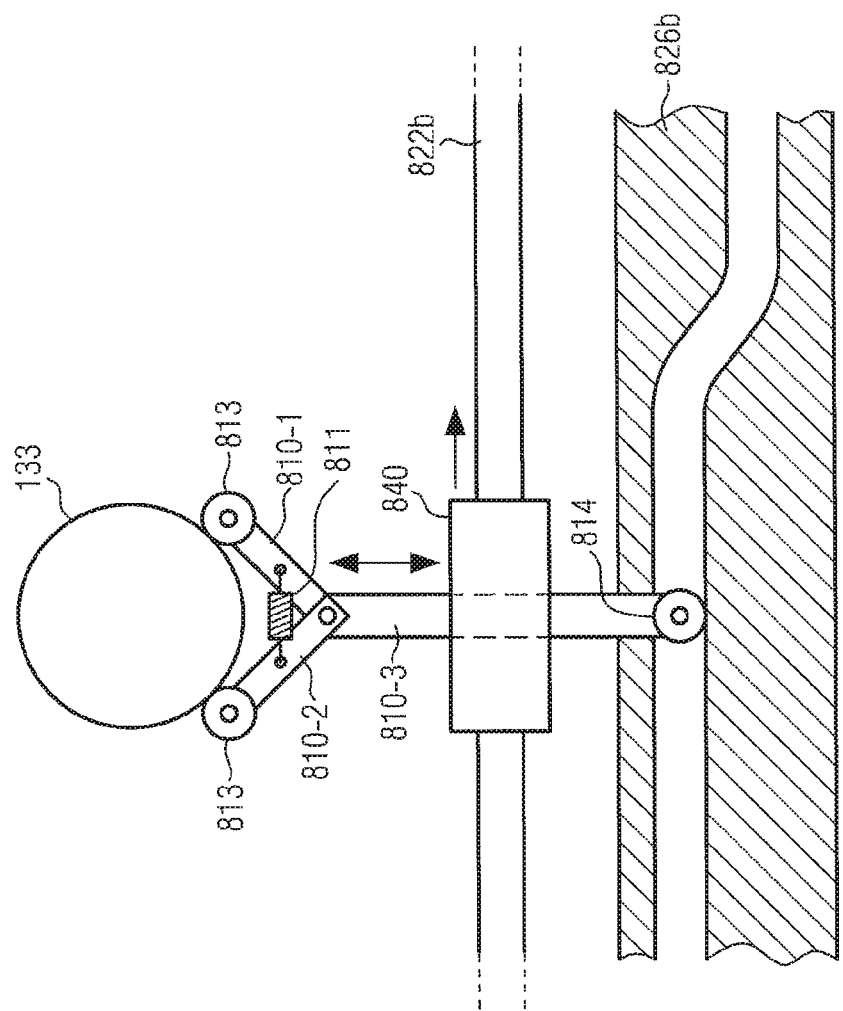
FIG. 8 shows an exemplary embodiment of a linearly displaceable holding device with end-mounted rollers.

FIG. 8 shows an exemplary embodiment of a linearly displaceable holding device with end-mounted rollers. According to this embodiment, the conveying unit 840 comprises a "long" leg 810-3 which is displaceable relative to the position of the conveying unit on the conveyor track 822*b* and on which the two "short" legs 810-1 and 810-2 of the Y-shaped holding device are supported in an angularly displaceable manner. In addition, the two "short" legs are connected to one another by a resilient element 811 in such a way that the legs can only be moved apart against the tension of this resilient element. Furthermore, the "short" legs 810-1 and 810-2 have arranged thereon the above-mentioned end-mounted rollers 813, which are adapted to be brought into contact with the surface of the container 133. The whole holding device can be moved up to the container, e.g. via the control curve 826*b* shown and the roller 814 running therein, such that the rollers will be pressed against the curved surface of the container and will thus be pushed apart. Provided that the rollers are suitably configured, e.g. rubber coated, it can thus be guaranteed that the conveyed containers will be held reliably. According to the further development shown here, the control curve 826*b* is configured such that the container 133 will be released towards the right, e.g. for discharge through a discharge conveying device.

Figure 9:
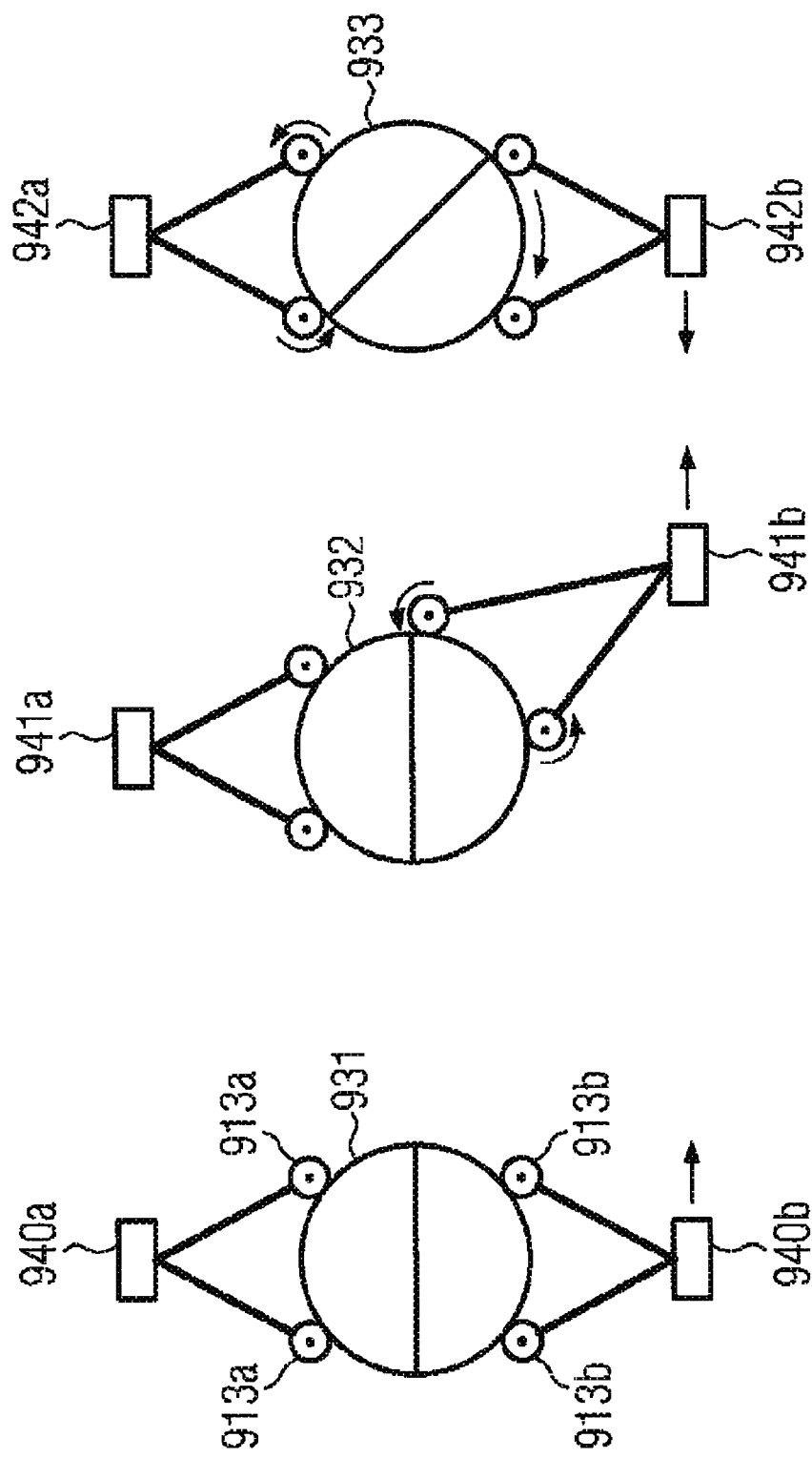
FIG. 9 shows schematically the rotation of a container by means of a ratchet mechanism.

FIG. 9 shows schematically how a container is rotated by means of a ratchet mechanism. The figure shows the rotation of the container by a predetermined (small) angle in three phases. A basic prerequisite for the use of the ratchet mechanism is that the end-mounted rollers 913*a* and/or the end-mounted rollers 913*b* of the holding devices of the oppositely engaging conveying units 940*a* and 940*b* are configured such that they will lock in one direction of rotation and rotate freely in the other direction of rotation. According to the further development shown here, the container is rotated when the conveying units are moved towards one another, with at least the rollers 913*b* locking in a clockwise direction. If, however, the conveying unit 940*a* is used as an active conveying unit for rotating the container, at least the rollers 913*a* will lock in an anticlockwise direction. Hence, the container can also be rotated when the conveying units are moved away from each other. In this case, the rollers 913*a* lock in a clockwise direction or the rollers 913*b* lock in an anticlockwise direction, depending on whether the conveying unit 940*a* or the conveying unit 940*b* is actively used for rotating the container.

According to the variant shown in FIG. 9, the conveying unit 940*b* is actively used for rotating the container 931. At the starting position shown on the left, the two conveying units 940*a* and 940*b* are arranged in opposed relationship with one another. By moving the conveying unit 941*b* faster than the conveying unit 941*a*, the two conveying units are moved apart, as shown in the middle of the figure. The rollers 913*b*, which rotate freely in an anticlockwise direction, roll on the surface of the container 932, which cannot participate in this rotating movement due to the fact that the rollers 913*a* lock in a clockwise direction. Only when the conveying units 942*a* and 942*b* are again moved towards each other, as shown on the right-hand side of the figure, the friction between the now locked rollers 913*b* and the surface of the container 933 will have the effect that also the container will be rotated. In this phase, the rollers 913*a*, which freely rotate in an anticlockwise direction, roll on the surface of the container. In order to achieve a larger angle of rotation, this process can be repeated until the angle of rotation has been accomplished. The arrows shown in the figure only show the relative movement of the conveying units, which may, of course, have superimposed thereon a general movement for conveying the container.

In order to be able to realize the ratchet mechanism, the holding devices of the conveying units are configured such that they are pivotable at least in a predetermined angular area and, optionally, such that they are linearly displaceable. The ratchet mechanism can thus be used for a large number of different container diameters. The relative displacement of the oppositely engaging conveying units can here be effected by an open-loop and/or closed-loop control unit of the conveyor arrangement in accordance with the diameter of the containers to be rotated.

The inspection devices described allow a reliable and individually controllable guidance of containers along the conveying route of the throughput station, so that, depending on the requirements to be fulfilled and on the type of containers, a desired speed and/or a desired inspection time of the containers can be predetermined. Thus, e.g. very strongly absorbing glass bottles that need a longer exposure time can dwell longer at the respective inspection station. In addition, the use of the individual drive allows individual containers to be picked up accurately from an infeed flow, even if the latter is conveyed under pressure, as well as to accurately predetermine a container pitch when the containers are transferred to the discharge flow, whereby complex devices for pressure reduction can be dispensed with in the incoming flow of containers.

The invention claimed is:

1. An inspection device for continuously inspecting fed containers, in particular bottles, comprising:
   a feed conveying device configured to feed containers to the inspection device in succession,
   at least one inspection unit configured to inspect the fed containers,
   a discharge conveying device configured to discharge the inspected containers, and
   a throughput station for the fed containers, which is arranged between the feed conveying device and the discharge conveying device,
   wherein
   the throughput station comprises a conveyor arrangement with an individual drive and a plurality of conveying units, which are movable by means of the individual drive individually and independently of one another, the conveyor arrangement being configured to convey the containers from the feed conveying device to the discharge conveying device;
   wherein the conveyor arrangement comprises a first conveyor track having movably arranged thereon a first plurality of conveying units, and a second conveyor track having movably arranged thereon a second plurality of conveying units,
   wherein the first conveyor track and the second conveyor track are arranged relative to one another and relative to the feed conveying device and the discharge conveying device such that, in the area of the throughput station, pairs of oppositely engaging conveying units for the containers are formed, said pairs consisting each of a conveying unit of the first plurality of conveying units and of a conveying unit of the second plurality of conveying units; and
   wherein the conveying units comprise laterally engaging holding devices, and wherein oppositely engaging conveying units of a pair are oriented relative to one another in the area of the throughput station such that at least one container is held and conveyed in a form-fit or in a force-fit manner between the holding devices of oppositely engaging conveying units such that a bottom area of the at least one container is freely accessible during conveyance.

2. The inspection device according to claim 1, wherein the holding devices comprise one or a plurality of Y-shaped clamps.

3. The inspection device according to claim 2,
   wherein a right angle is provided between the Y-legs of the clamps; and/or
   wherein the holding devices are arranged on the conveying units in a linearly displaceable manner.

4. The inspection device according to claim 2, wherein the plurality of Y-shaped clamps are provided with end mounted rollers.

5. The inspection device according to claim 1, wherein the holding devices are pivotable.

6. The inspection device according to claim 1,
   wherein the individual drive is a linear motor drive,
   wherein the conveying units are configured as carriages, which are movable individually and independently of one another via magnetic interaction with the linear motor drive, and
   wherein the conveyor arrangement additionally comprises an open-loop and/or closed-loop control unit, which is configured to move the conveying units from a pick-up site for the containers at the feed conveying device to a discharge site for the containers at the discharge conveying device.

7. The inspection device according to claim 6, wherein the open-loop and/or closed-loop control unit is configured to move the conveying units of the first plurality of conveying units at least along part of the throughput station at a speed which is higher than that of the conveying units of the second plurality of conveying units.

8. The inspection device according to claim 1, further comprising a first inspection station arranged near the feed conveying device and configured to inspect the fed containers passing the first inspection station from the side, and/or a second inspection station arranged near the discharge conveying device and configured to inspect the passing fed containers passing the second inspection station from the side.

9. The inspection device according to claim 8, wherein the first and/or second inspection station(s) comprise(s) an optical system with a camera, said optical system being configured such that the side of the container to be inspected is detected within a predetermined angular area.

10. The inspection device according to claim 9, wherein the angular area of the first inspection station is smaller than the angular area of the second inspection station.

11. The inspection device according to claim 1, further comprising a bottom inspection station in an area of the throughput station said bottom inspection station being configured to inspect bottoms of the fed containers passing the bottom inspection station.

12. A method of continuously inspecting containers, in particular bottles, comprising the following steps:
   successive feeding of containers to a throughput station of an inspection device,
   conveying the fed containers in the throughput station, inspecting the fed containers in the throughput station, and discharging the inspected fed containers that are inspected, wherein the fed containers are conveyed in the throughput station by means of a conveyor arrangement comprising an individual drive and a plurality of conveying units movable individually and independently of one another by means of the individual drive, wherein the fed containers are conveyed in the throughput station by means of oppositely engaging conveying units and are, while being conveyed, held in a form-fit or in a force-fit manner between laterally engaging holding devices of the oppositely engaging conveying units such that a bottom area of the conveyed containers is freely accessible during conveyance.

13. The method according to claim 12, wherein the individual drive is a linear motor drive, and wherein the conveying units are configured as carriages, which are movable in a controlled manner through magnetic interaction with the linear motor drive.

14. The method according to claim 12, wherein the containers are fed to the conveyor arrangement in a mutually abutting mode.

* * * * *